US012761221B2

(12) United States Patent
Zander et al.

(10) Patent No.: US 12,761,221 B2
(45) Date of Patent: Oct. 13, 2026

(54) METHOD FOR DETERMINING LUPUS ANTICOAGULANT IN A SINGLE COAGULATION REACTION

(71) Applicant: Siemens Healthcare Diagnostics Products GmbH, Marburg (DE)

(72) Inventors: Norbert Zander, Marburg (DE); Carina Gerlach, Dautphetal (DE); Michael Timme, Coelbe (DE); Regina Gebauer, Rabenau (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 1262 days.

(21) Appl. No.: 17/671,870

(22) Filed: Feb. 15, 2022

(65) Prior Publication Data

US 2022/0260564 A1 Aug. 18, 2022

(30) Foreign Application Priority Data

Feb. 16, 2021 (EP) .................................... 21157263

(51) Int. Cl.
*G01N 33/564* (2006.01)
*G01N 21/77* (2006.01)
*G01N 35/00* (2006.01)

(52) U.S. Cl.
CPC ........... *G01N 33/564* (2013.01); *G01N 21/77* (2013.01); *G01N 35/00029* (2013.01); *G01N 35/00584* (2013.01); *G01N 2800/104* (2013.01)

(58) Field of Classification Search
CPC ........... G01N 21/77; G01N 2021/7783; G01N 35/00584; G01N 33/4905; G01N 33/564; G01N 33/86; G01N 2800/104; G01N 2800/224
USPC ........................................................... 436/69
See application file for complete search history.

(56) References Cited

U.S. PATENT DOCUMENTS

| | | | | |
|---|---|---|---|---|
| 10,215,766 | B2 | 2/2019 | Shima et al. | |
| 2003/0104493 | A1 | 6/2003 | Braun et al. | |
| 2016/0178651 | A1 | 6/2016 | Shima et al. | |
| 2016/0291042 | A1 | 10/2016 | Kumano et al. | |
| 2021/0333295 | A1 | 10/2021 | Kawabe et al. | |
| 2022/0146537 | A1* | 5/2022 | Kawabe ............. | G01N 33/4905 |

FOREIGN PATENT DOCUMENTS

| | | | |
|---|---|---|---|
| EP | 3076178 | A1 | 10/2016 |
| JP | 2016118442 | A | 6/2016 |
| JP | 2019086518 | A | 6/2019 |
| WO | 2020101025 | A1 | 5/2020 |

OTHER PUBLICATIONS

Gschwandtner, M. E. et al, Blood Coagulation & Fibrinolysis 1996, 7, 325-330. (Year: 1996).*
Eschwege, V. et al, Thrombosis and Haemostasis 1996, 76, 65-68. (Year: 1996).*

(Continued)

*Primary Examiner* — Arlen Soderquist
(74) *Attorney, Agent, or Firm* — BakerHostetler

(57) ABSTRACT

The invention is in the field of coagulation diagnostics and relates to a method for detecting lupus anticoagulant.

7 Claims, 1 Drawing Sheet

(56) References Cited

OTHER PUBLICATIONS

Cloherty, T. et al, Thrombosis Research 1996, 83, 137-142. (Year: 1996).*
Braun, P. J. et al, Thrombosis and Haemostasis 1997, 78, 1079-1087. (Year: 1997).*
Givens, T. B. et al, International Journal of Medical Informatics 1997, 46, 129-143. (Year: 1997).*
Mackie, I. J. et al, in "Hughes Syndrome" Khamashta, M. A. (ed.), Springer-Verlag, London 2000, 214-224. (Year: 2000).*
de Pablo, P. et al, Clinical and Applied Thrombosis/Hemostasis 2003, 9, 221-225. (Year: 2003).*
Tripodi, A., Clinical Chemistry 2007, 53, 1629-1635. (Year: 2007).*
Sorensen, B. et al, Journal of Thrombosis and Haemostasis 2012, 10, 244-250. (Year: 2012).*
Fritsma, G. A. et al, American Journal of Clinical Pathology 2012, 137, 904-908. (Year: 2012).*
Shima, M. et al, Journal of Thrombosis and Haemostasis 2013, 11, 1417-1420 with 6 pages of supporting information. (Year: 2013).*
Kumano, O. et al, Thrombosis Research 2014, 134, 503-509. (Year: 2014).*
Xu, X. et al, IEEE Journal of Selected Topics in Quantum Electronics 2016, 22, 197-202. (Year: 2016).*
Moore, G. W., Antibodies 2016, 5, Article 22, 15 pages. (Year: 2016).*
Matsumoto, T. et al, International Journal of Hematology 2017, 105, 174-183. (Year: 2017).*
Hoxha, A. et al, Autoimmunity Reviews 2017, 16, 173-178. (Year: 2017).*
Smith, L. J., Clinical Laboratory Science 2017, 30, 7-14. (Year: 2017).*
Seheult, J. N. et al, American Journal of Clinical Pathology 2017, 147, 632-640. (Year: 2017).*
Ruberto, M. F. et al, Clinical Chemistry and Laboratory Medicine 2018, 56, 448-453. (Year: 2018).*
Kumano, O. et al, International Journal of Laboratory Hematology 2019, 41, 60-68. (Year: 2019).*
Shimomura, D. et al, Clinical and Applied Thrombosis/Hemostasis 2020, 26, 1-8. (Year: 2020).*
Tripodi, A. et al, Journal of Thrombosis and Haemostasis 2020, 18, 1569-1575. (Year: 2020).*
Bowles, L. et al, New England Journal of Medicine, 2020, 383, 288-290 with 9 pages of supplemental index. (Year: 2020).*
Reda, S. et al, Scientific Reports 2020, 10, Article 12221, 9 pages. (Year: 2020).*
Devreese, K. M. J. et al, Journal of Thrombosis and Haemostasis 2020, 18, 2828-2839. (Year: 2020).*
Velasco-Rodríguez, D. et al, Thrombosis Research 2020, 196, 425-431. (Year: 2020).*
Fan, B. E. et al, Journal of Thrombosis and Thrombolysis 2021, 51, 663-674. (Year: 2021).*
Shimonishi, N. et al, Thrombosis and Haemostasis 2021, 121, 792-799. (Year: 2021).*
Kanouchi, K. et al, Health Science Reports 2021, 4, Article e258, 7 pages. (Year: 2021).*
Anonymous: "Coagpia (TM) APTT-N"; 1. Apr. 2011 (Apr. 1, 2011); pp. 1-2; XP055823530; Gefunden im Internet: URL:https://manualzz.com/doc/6930596/coagpia%E2%84%A2aptt-n; [gefunden am Jul. 12, 2021]; * das ganze Dokument *.
Kumano, Osamu et al: "Lupus anticoagulant mixing tests for multiple reagents are more sensitive if interpreted with a mixing test-specific cut-off than index of circulating anticoagulant"; Research and Practice in Thrombosis and Haemostasis; vol. 2; No. 1; 1. Jan. 2018 (Jan. 1, 2018); pp. 105-113; XP055823219.
Shimonishi, Naruto et al: "A Novel Assessment of Factor VIII Activity by Template Matching Utilizing Weighted Average Parameters from Comprehensive Clot Waveform Analysis", Thrombosis and Haemostasis; vol. 121; No. 02; 22. Aug. 2020 (Aug. 22, 2020); pp. 164-173; XP055823241.
Nogami K. et al: "Nodi fi ed clot waveform analysis to measure plasma coagulation potential in the presence of the anti-factor IXa/factor X bispecific antibody emicizumab"; Journal of Thrombosis and Haemostasis; vol. 16; No. 6; 13. Mai 2018 (May 13, 2018); pp. 1078-1088; XP055822685.
Devreese K, et al; "Challenges in the Diagnosis of the Antiphospholipid Syndrome"; Clinical Chemistry; Bd. 56 Nr.6; pp. 930-940; ISSN: 009-9147; DOI: 10.1373/clinchem.2009.133678; XP055032492; 2010.
Antiphospholipid syndrome, Health Portal, https://www.gesundheit.gv.at/labor/laborwerte/blutgerinnung/labor-aptt-lupus-sensitiv-apttl3.html, Dec. 2019, pp. 1-5.
Kumano et al., APTT reagent with ellagic acid as activator shows adequate lupus anticoagulant sensitivity in comparison to silica-based reagent, Journal of Thrombosis and Haemostasis, 2012, pp. 2338-2343, vol. 10, DOI: 10.1111/j.1538-7836.2012.04906.x.
Dade® Actin® FSL Activated PTT Reagent, Siemens Healthcare Diagnostics Products GmbH, 2024, pp. 1-10, Sysmex, Marburg, Germany.

* cited by examiner

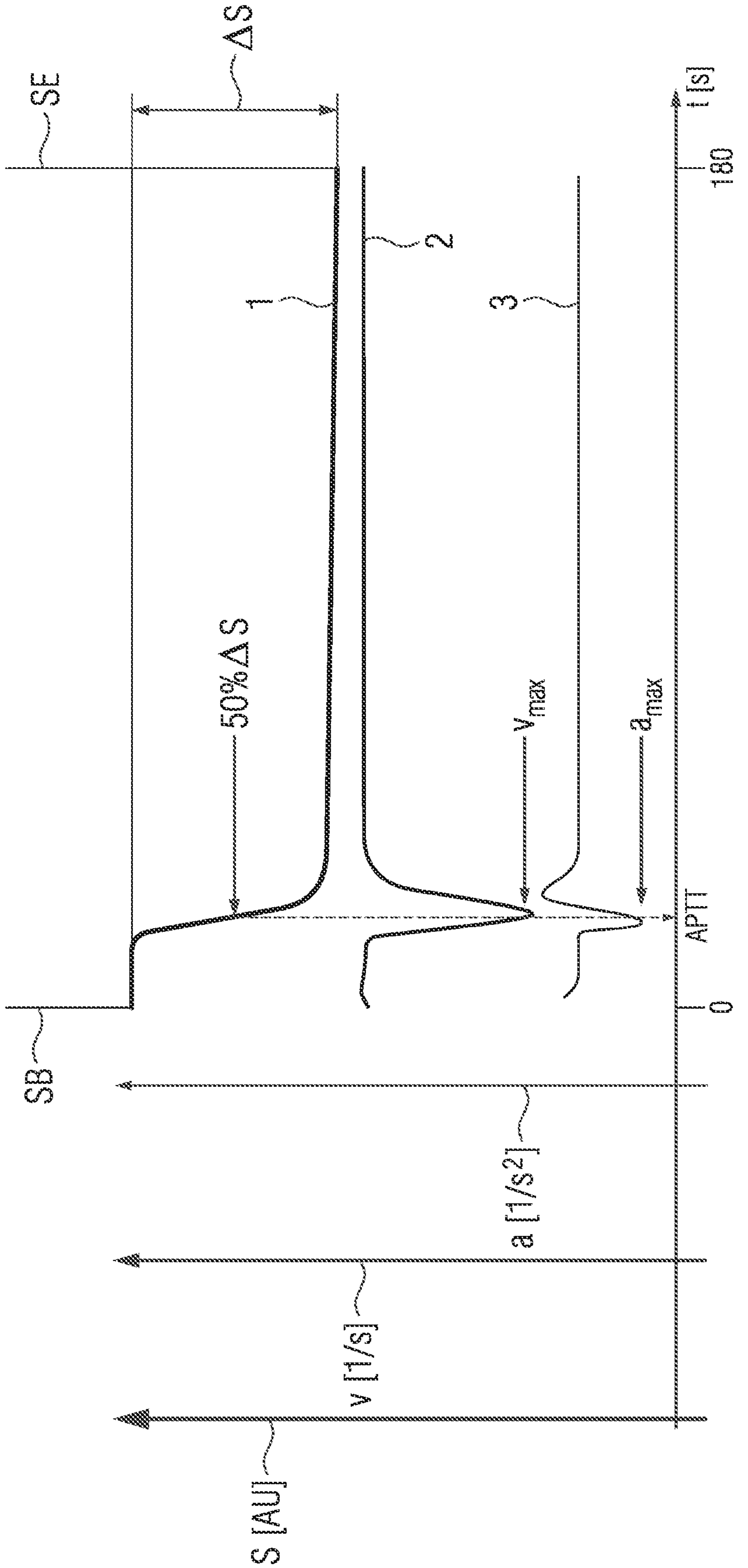
SE
ΔS
t [s]
180
0
1
2
3
50%ΔS
$v_{max}$
$a_{max}$
APTT
SB
a [1/s$^2$]
v [1/s]
S [AU]

METHOD FOR DETERMINING LUPUS ANTICOAGULANT IN A SINGLE COAGULATION REACTION

CROSS-REFERENCE TO RELATED APPLICATIONS

This application claims priority to and benefit of EP Application No. 21157263.1, filed Feb. 16, 2021. The entire disclosure of the foregoing application is incorporated by reference herein.

The invention is in the field of coagulation diagnostics and relates to a method for detecting lupus anticoagulant.

Lupus anticoagulants (LA) are immunoglobulins and belong to the type of acquired autoantibodies. They cause antiphospholipid syndrome (APS), one of the most common autoimmune diseases, and elicit thromboses, recurrent miscarriages, and complications during pregnancy. Lupus anticoagulant immunoglobulins are so-called antiphospholipid antibodies (APA), which bind to anionic phospholipids, to proteins or to protein/phospholipid complexes. Antiphospholipid antibodies, which form complexes with certain proteins and phospholipids, are a very heterogeneous group of autoantibodies which can be directed against a multiplicity of antigens, such as, for example, against the apolipoprotein β2-glycoprotein I (β2GPI), cardiolipin, prothrombin, protein C, protein S, thrombomodulin, factor XII and others, and against complexes of these proteins with phospholipids.

So-called lupus anticoagulants are antiphospholipid antibodies which, by definition, prolong the coagulation times of certain coagulation tests, of APTT for example. Paradoxically, lupus anticoagulants bring about inhibition of the coagulation reaction in vitro, whereas, in vivo, an increased coagulation reaction (hypercoagulability) is associated with antiphospholipid syndrome (APS).

Laboratory diagnosis of antiphospholipid syndrome (APS) is complicated by the heterogeneity of antiphospholipid antibodies. For direct detection of the antibodies, immunological methods are used. However, many antibodies which do not have prothrombotic action in vivo are also detected here. For indirect, functional detection of the antibodies, coagulation tests are used. In a coagulation test, a plasma sample of the patient is typically mixed with a coagulation activator, phospholipids and calcium ions, and what is measured is the time until clot formation. Particularly tests based on the determination of DRVVT (dilute Russell's viper venom time) show a relatively good correlation with the prothrombotic efficacy of antiphospholipid antibodies. Lupus diagnostics is very complex because each patient sample has to pass through multiple analysis steps (for a review, see: Devreese, K. and Hoylaerts, M. F., Challenges in the diagnosis of the antiphospholipid syndrome. Clin. Chem. 2010, 56(6): 930-940).

Typically, a patient sample is analysed using two variants of at least one coagulation test in order to diagnose a lupus anticoagulant. In the first variant, which is sensitive to lupus anticoagulant, the test is carried out in the presence of a relatively low concentration of phospholipid (screening test); in the second variant, which is insensitive to lupus anticoagulant, the same test is carried out in the presence of a relatively high concentration of phospholipid (confirmation test). A prolonged coagulation time, compared to normal samples (which do not contain lupus anticoagulant), in the first test variant (screening test) in combination with a normal coagulation time, compared to normal samples, in the second test variant (confirmation test) indicates the presence of lupus anticoagulant.

A particularly commonly used test is the DRVVT test, with the first variant sensitive to lupus anticoagulant being carried out with an activation reagent containing Russell's viper venom and a relatively low concentration of phospholipid (LA1 screening reagent) and the second variant insensitive to lupus anticoagulant being carried out with an activation reagent containing Russell's viper venom and a high concentration of phospholipid (LA2 confirmation reagent). If the LA1 test is negative, i.e. there is no measurement of a prolonged coagulation compared to the comparison standard, it is no longer necessary to carry out the LA2 test. Another commonly used test is the APTT test.

It is thus disadvantageous that the indirect, functional detection of lupus anticoagulant always requires that at least two coagulation tests be carried out, which is associated with an increase in the materials, time and work required.

It is an object of the present invention to provide a method for indirect, functional detection of lupus anticoagulant in a body fluid sample, which method avoids the aforementioned disadvantages.

It has been found that it is possible to detect lupus anticoagulant by determination of the coagulation time and evaluation of certain parameters of the reaction curve of a single coagulation reaction carried out with a lupus anticoagulant-sensitive APTT reagent.

The present invention thus provides a method for detecting lupus anticoagulant in a plasma sample of a patient. The method comprises the following steps:

- providing a reaction mixture by addition of a lupus anticoagulant-sensitive APTT reagent to the plasma sample and starting the coagulation reaction,
- measuring a measurement variable S of the reaction mixture over time (t), resulting in a function S(t) of time-dependent measurement values, and
- determining the coagulation time.

According to the invention, what are additionally carried out in the method are that a) the maximum reaction velocity $v_{max}$ and/or the maximum reaction acceleration $a_{max}$ of the function S(t) are determined, and b) the absolute value of the difference between a first measurement value SB at the start of measurement and a second measurement value SE at the end of measurement (|DeltaS|) is ascertained, and then c) the relative maximum reaction velocity $v_{max\ rel}$ and/or the relative maximum reaction acceleration $a_{max\ rel}$ are determined using the following formulae:

$$v_{max\,rel} = v_{max} / |DeltaS| \text{ and}$$

$$a_{max\,rel} = a_{max} / |DeltaS|, \text{ respectively.}$$

Lupus anticoagulant is ultimately detected if the coagulation time is prolonged compared to a predetermined reference value and the relative maximum reaction velocity $v_{max\ rel}$ and/or the relative maximum reaction acceleration $a_{max\ rel}$ are within a predetermined lupus anticoagulant-specific range of values.

The plasma sample of a patient is preferably a low-platelet-count plasma sample of a person. Preferably, the low-platelet-count plasma sample is obtained from citrated whole blood.

APTT (activated partial thromboplastin time) is a test to check the intrinsic blood coagulation system. An APTT reagent, which is added to a sample to be tested, typically contains phospholipids ("partial thromboplastins"), a surface-active substance (a so-called "contact activator"), such as, for example, ellagic acid, kaolin or silica, and optionally calcium ions. A lupus anticoagulant-sensitive APTT reagent typically contains a reduced concentration of phospholipids, compared to a lupus anticoagulant-insensitive APTT reagent, meaning that measurement of the coagulation time of lupus anticoagulant-containing samples using such a reagent leads to a prolonged coagulation time, compared to normal (lupus anticoagulant-free) samples. Lupus anticoagulant-sensitive APTT reagents can contain further components, such as, for example, certain divalent metal ion-producing substances, which boost the effect of the coagulation time-prolonging action (see, for example, EP 3076178 A1). Alternatively, the calcium ions can be provided in a separate reagent, which is added to the sample to be tested in addition to the lupus anticoagulant-sensitive APTT reagent. The addition of the calcium ions starts the coagulation reaction in the reaction mixture.

The measurement of a measurement variable S of the reaction mixture over time (t), resulting in a function S(t) of time-dependent measurement variables, typically begins with the addition of or immediately or shortly after the addition of the calcium ions.

Typical measurement variables S of the reaction mixture which change over time as a consequence of the coagulation reaction are, for example, the turbidity or the viscosity of the reaction mixture as a consequence of fibrin formation in the reaction mixture, and they can be determined quantitatively with the aid of optical or mechanical methods. Continuous determination of the measurement variable over a certain period results in a function S(t) of time-dependent measurement values, i.e. a reaction curve. Depending on the nature of the measurement variable, a measurement variable can change proportionally or inversely proportionally to the coagulation reaction.

The determination of the coagulation time of the reaction mixture can be carried out with any conventional evaluation method. Typically, the term "coagulation time" is understood to mean the time span from the start of the coagulation reaction by addition of the relevant reagents to the sample up to the tangible formation of a fibrin clot in seconds. The coagulation time is preferably determined on the basis of the reaction curve and a suitable evaluation method.

The coagulation time determined for the sample or the reaction mixture is compared with a predetermined reference value which distinguishes a normal coagulation time from a prolonged coagulation time. Said reference value is determined beforehand by, for example, determining the coagulation time for a statistically significant number of normal (lupus anticoagulant-free) plasma samples and/or for one or more normal plasma pools using the lupus anticoagulant-sensitive APTT reagent.

The maximum reaction velocity $v_{max}$ of the function S(t) can be determined by—depending on whether the measurement variable changes proportionally or inversely proportionally to the coagulation reaction—determining the maximum or the minimum of the first derivative (dS(t)/dt) of the function S(t).

The maximum reaction acceleration $a_{max}$ of the function S(t) can be determined by—depending on whether the measurement variable changes proportionally or inversely proportionally to the coagulation reaction—determining the maximum or the minimum of the second derivative ($d^2 S(t)/dt^2$) of the function S(t).

Furthermore, the absolute value of the difference between a first measurement value SB at the start of measurement and a second measurement value SE at the end of measurement (|DeltaS|) is ascertained. As is generally known, a coagulation reaction proceeds essentially in three phases. In the first phase, at the start of measurement, i.e. from the time point in which the sample has been mixed with the coagulation-time reagent and calcium ions and the coagulation reaction has thus been started, no significant change in signal, i.e. no change in the measurement variable 5, can be identified over a certain period, i.e. the reaction curve runs substantially parallel to the x-axis (t). In the subsequent second phase, what can be identified is a change in signal, the rate of change of which first increases before decreasing after a maximum has been reached. In the subsequent third phase, at the end of measurement, the signal level has reached a maximum, and there is no longer any further change in signal, i.e. the reaction curve again runs parallel to the x-axis (t), though at a signal level different to in the first phase. The first measurement value SB is thus a measurement value from the first phase of the coagulation reaction; the second measurement value SE is thus a measurement value from the third phase of the coagulation reaction. Both the first measurement value SB and the second measurement value SE can be, in each case, an individual measurement value or a mean of multiple (e.g. 2, 3, 4, 5 or more) successive measurement values within the respective reaction phase.

Furthermore, a check is made as to whether the relative maximum reaction velocity $v_{max\ rel}$, determined for the sample or the reaction mixture, and/or the relative maximum reaction acceleration $a_{max\ rel}$ are within a predetermined lupus anticoagulant-specific range of values. Said lupus anticoagulant-specific range of values is determined beforehand by, for example, starting the coagulation reaction in a statistically significant number of lupus anticoagulant-containing plasma samples and normal (lupus anticoagulant-free) plasma samples (and/or for one or more normal plasma pools) by addition of the lupus anticoagulant-sensitive APTT reagent, measuring a measurement variable S of the reaction mixture over time (t), which results in a function S(t) of time-dependent measurement values, and then determining the relative maximum reaction velocity $v_{max\ rel}$ and/or the relative maximum reaction acceleration $a_{max\ rel}$—as described above in steps a) to c). What can be determined in this way is a range of values which is specific for lupus anticoagulant-containing samples.

It has been found that, by means of the method according to the invention, lupus anticoagulant-containing samples can be reliably differentiated from normal samples and from samples containing other factors which prolong coagulation time, such as, for example, heparin, coagulation factor deficiency and direct oral anticoagulants. It is particularly advantageous that the evaluation of a single coagulation reaction allows this differentiation, with the result that a second coagulation reaction containing a different reagent, as required according to the prior art, can be dispensed with.

The present invention further provides an automatic analyser configured such that it carries out the above-described method according to the invention.

Known automatic analysers intended for the automatic processing and evaluation of coagulation tests comprise at least (i) one or more pipetting devices for transfer of a sample volume and at least one reagent volume into a reaction vessel for preparation of a reaction mixture, (ii) a measurement device for measurement of a measurement variable S of the reaction mixture in the reaction vessel over time (t), (iii) a data memory for storage of a function S(t) of time-dependent measurement values which were measured for a sample or a reaction mixture, and (iv) an evaluation device configured such that it uses the function S(t) of time-dependent measurement values from the data memory for calculation of a coagulation time.

An automatic analyser according to the invention is distinguished by the evaluation device being additionally configured such that it a) determines the maximum reaction velocity $v_{max}$ and/or the maximum reaction acceleration $a_{max}$ of the function S(t), and
b) ascertains the absolute value of the difference between a first measurement value SB at the start of measurement and a second measurement value SE at the end of measurement (|DeltaS|), and then
c) determines the relative maximum reaction velocity $v_{max\ rel}$ and/or the relative maximum reaction acceleration $a_{max\ rel}$ using the following formulae:

$$v_{max\,rel} = v_{max} / |DeltaS| \text{ and}$$

$$a_{max\,rel} = a_{max} / |DeltaS|, \text{ respectively,}$$

d) compares the determined coagulation time with a predetermined reference value, and
e) compares the relative maximum reaction velocity $v_{max\ rel}$ and/or the relative maximum reaction acceleration $a_{max\ rel}$ with a respectively predetermined lupus anticoagulant-specific range of values, and
f) outputs the presence of lupus anticoagulant in the sample as the result if the coagulation time is prolonged compared to the predetermined reference value and the relative maximum reaction velocity $v_{max\ rel}$ and/or the relative maximum reaction acceleration $a_{max\ rel}$ are within the respective predetermined lupus anticoagulant-specific range of values.

The result of the presence of lupus anticoagulant in the sample is preferably output to a display medium, for example a monitor, a mobile device or a printer, by means of which the result can be communicated to a user.

The measurement device for measurement of a measurement variable S of the reaction mixture can be a device for measurement of an optical property, such as, for example, absorption, for example a photometer.

DESCRIPTION OF FIGURE

FIG. 1 shows a typical APTT coagulation curve on a Sysmex CS-2100 analyser. Curve 1 shows the optical transmissivity/transmission (S) of the reaction mixture in artificial units [AU] over time, over a period of 180 s. The difference Delta S (ΔS) between the transmissivities at the end of measurement (measurement value SE at time point t=180 s) and at the start of measurement (measurement value SB at time point t=0 s) can be read in the software. The APTT coagulation time is determined by determining the time point in which the measurement value corresponds to 50% of the difference Delta S (ΔS). Curve 2 shows the numerical 1st derivative with respect to time (dS/dt), which is a measure of the velocity v of the reaction. It has a minimum at the highest reaction velocity $v_{max}$. Curve 3 shows the numerical 2nd derivative with respect to time ($d^2S/dt^2$), which is a measure of the acceleration a of the reaction. It has a minimum at the highest reaction acceleration $a_{max}$—The numerical values for the maximum reaction velocity $v_{max}$ and the maximum reaction acceleration $a_{max}$ can be read via the software. The numerical values for the relative maximum velocity $v_{max\ rel}$ and the relative maximum acceleration $a_{max\ rel}$ are yielded by division of the absolute values for maximum velocity and maximum acceleration by the absolute value of Delta S.

The invention will be elucidated below on the basis of an exemplary embodiment.

Example: Identification of Lupus Anticoagulant-Positive Samples in a Single APTT Coagulation Mix in Each Case in Accordance with the Invention The following types of low-platelet-count plasma samples were tested:

| Sample type | Description |
|---|---|
| Normal | Pool of >100 donations from healthy individuals, stabilized; |
| Heparin | Pool of >100 donations from healthy individuals, stabilized and admixed with unfractionated or low-molecular-weight heparin (UF or LMW heparin); |
| Factor VIII deficiency | Mixture of factor VIII-deficient plasma and normal pool; |
| Lupus anticoagulant (LA) | Plasmas from individual donors, lupus anticoagulant-positive in a test system based on the dilute Russell's viper venom (DRVVT) test. |

For the measurement of APTT, the test setting approved on the Sysmex CS-2100 analyser (Sysmex Corp.) is used. 50 µL of sample are mixed with 50 µL of lupus anticoagulant-sensitive APTT reagent (Actin FSL reagent, Siemens Healthcare Diagnostics Products GmbH) containing phospholipids and ellagic acid as activator. After 180 s of incubation at +37° C., 50 µL of 25 mM $CaCl_2$ are added to start the reaction, and the acquisition of measurement values is started.

The APTT coagulation time is determined by ascertaining the time point at which the measured optical transmissivity of the reaction mixture is 50% of the difference Delta S between the transmissivities at the end of measurement (measurement value SE at time point t=180 s) and at the start of measurement (measurement value SB at time point t=0 s). Coagulation time results of more than 30 s are considered prolonged.

The relative maximum reaction velocity $v_{max\ rel}$ is determined by first ascertaining the maximum reaction velocity $v_{max}$ by determination of the minimum of the 1st derivative of the reaction kinetics with respect to time (dS/dt) and lastly dividing $v_{max}$ by the absolute value of Delta S.

The relative maximum reaction acceleration $a_{max\ rel}$ is determined by first ascertaining the maximum reaction acceleration $a_{max}$ by determination of the minimum of the 2nd derivative of the reaction kinetics with respect to time ($d^2S/dt^2$) and lastly dividing $a_{max}$ by the absolute value of Delta S.

The results for each sample are shown in Table 1.

TABLE 1

| Sample | APTT [s] | $v_{max\ rel}$ [$10^{-3}$ $s^{-1}$] | $a_{max\ rel}$ [$10^{-5}$ $s^{-2}$] |
|---|---|---|---|
| Normal 1 | 24.8 | 7.0 | 11.3 |
| Normal 2 | 27.3 | 6.9 | 11.1 |
| LMW heparin, 1.0 IU/mL | 50.4 | 3.9 | 5.2 |
| UF heparin, 0.6 IU/mL | 75.2 | 2.7 | 2.7 |
| Factor VIII deficiency 1, 5% | 46.7 | 2.7 | 2.8 |
| Factor VIII deficiency 2, 5% | 43.2 | 3.7 | 4.6 |
| LA 1 | 51.6 | 1.3 | 1.5 |
| LA 2 | 40.9 | 1.7 | 2.3 |
| LA 3 | 37.4 | 1.2 | 1.6 |
| LA 4 | 36.7 | 1.2 | 1.7 |
| LA 5 | 31.7 | 1.1 | 1.6 |
| LA 6 | 35.8 | 1.5 | 2.2 |
| LA 7 | 36.7 | 1.2 | 1.5 |
| LA 8 | 80.2 | 2.3 | 2.3 |
| LA 9 | 69.1 | 1.9 | 2.0 |
| LA 10 | 51.9 | 1.1 | 1.3 |

As expected, prolonged coagulation times (>30 s) are exhibited by heparin samples, factor VIII-deficient samples (having a deficiency of a factor of the intrinsic system) and lupus anticoagulant-positive samples, whereas normal samples do not exhibit prolonged coagulation times. As screening test for lupus anticoagulant, the APTT in this experiment has a sensitivity of 100%.

For lupus anticoagulant-positive samples, it becomes apparent, furthermore, that the above-described parameter $v_{max\ rel}$ is in a range of values from 1.1 to 2.3 $10^{-3}$ $s^{-1}$, which range is specific for lupus anticoagulant-positive samples. Furthermore, it becomes apparent for lupus anticoagulant-positive samples that the parameter $a_{max\ rel}$, likewise described above, is in a range of values from 1.3 to 2.3 $10^{-5}$ $s^{-2}$, which range is likewise specific for lupus anticoagulant-positive samples. Other samples (normal samples, heparin samples, factor VIII-deficient samples) each have greater numerical values for the parameters $v_{max\ rel}$ and $a_{max\ rel}$, which numerical values are outside the lupus anticoagulant-specific ranges of values for $v_{max\ rel}$ and $a_{max\ rel}$.

Therefore, a two-step method which originates from only a single APTT measurement and comprises the determination of coagulation time and the determination of the parameters $v_{max\ rel}$ and/or $a_{max\ rel}$ is suitable as proof for lupus anticoagulant.

In the present experiment, the method for detecting lupus anticoagulant has a sensitivity of 100% and a specificity of 100%.

The invention claimed is:

1. A method for detecting a lupus anticoagulant in a reaction mixture, the method comprising the steps of:

(i) preparing a reaction mixture by combining a plasma sample of a patient with a lupus anticoagulant-sensitive activated partial thromboplastin time (APTT) reagent, which reagent contains ellagic acid and phospholipids and leads to prolonged coagulation time measurements in lupus anticoagulant-containing samples compared to coagulation time measurements in normal, lupus anticoagulant-free samples in a reaction vessel, and starting the coagulation reaction, (ii) continuously measuring a measurement variable S of the reaction mixture over time, resulting in a function S(t) of time-dependent measurement values for the reaction mixture, and (iii) determining the coagulation time for the reaction mixture, characterized in that a) the maximum reaction velocity $v_{max}$ and/or the maximum reaction acceleration $a_{max}$ of the function S(t) for the reaction mixture are determined, b) the absolute value of the difference between a first measurement value SB at the start of measurement and a second measurement value SE at the end of measurement (|DeltaS|) is ascertained for the reaction mixture, and c) a relative maximum reaction velocity $v_{max\ rel}$ and/or a relative maximum reaction acceleration $a_{max\ rel}$ for the reaction mixture are determined using the following formulae:

$$v_{max\,rel} = v_{max} / |DeltaS| \text{ and}$$

$$a_{max\,rel} = a_{max} / |DeltaS|,$$

respectively, and (iv) detecting the lupus anticoagulant in the reaction mixture when the coagulation time of the reaction mixture is prolonged compared to a predetermined reference value, and the relative maximum reaction velocity $v_{max\ rel}$ value and/or the relative maximum reaction acceleration $a_{max\ rel}$ value for the reaction mixture are within a predetermined lupus anticoagulant-specific range of value(s) for the reaction mixture.

2. The method according to claim 1, wherein the lupus anticoagulant-sensitive APTT reagent additionally contains calcium ions.

3. The method according to claim 1, wherein the maximum reaction velocity $v_{max}$ corresponds to the maximum or the minimum of the first derivative of the function S(t) of the time-dependent measurement values.

4. The method according to claim 1, wherein the maximum reaction acceleration $a_{max}$ corresponds to the maximum or the minimum of the second derivative of the function S(t) of the time-dependent measurement values.

5. The method of claim 1, wherein the reaction mixture in the reaction vessel is incubated prior to starting the coagulation reaction.

6. The method of claim 1, wherein the coagulation reaction is started by adding calcium ions to the reaction mixture.

7. The method of claim 6, wherein the calcium ions are in the form of calcium chloride.

* * * * *